(12) United States Patent
Ginn (10) Patent No.: US 7,361,183 B2
(45) Date of Patent: Apr. 22, 2008

(54) LOCATOR AND DELIVERY DEVICE AND METHOD OF USE

(75) Inventor: Richard S. Ginn, San Jose, CA (US)

(73) Assignee: Ensure Medical, Inc., Sunnyvale, CA (US)

( * ) Notice: Subject to any disclaimer, the term of this patent is extended or adjusted under 35 U.S.C. 154(b) by 495 days.

(21) Appl. No.: 10/850,795

(22) Filed: May 21, 2004

(65) Prior Publication Data

US 2005/0085856 A1   Apr. 21, 2005

Related U.S. Application Data

(63) Continuation-in-part of application No. 10/687,848, filed on Oct. 17, 2003.

(51) Int. Cl.
*A61M 29/00* (2006.01)
(52) U.S. Cl. .................. 606/194; 606/213; 128/887
(58) Field of Classification Search .................. None
See application file for complete search history.

(56) References Cited

U.S. PATENT DOCUMENTS

| 5,007,921 | A |   | 4/1991  | Brown |
|---|---|---|---|---|
| 5,021,059 | A |   | 6/1991  | Kensey et al. |
| 5,026,390 | A |   | 6/1991  | Brown |
| 5,061,274 | A | * | 10/1991 | Kensey .................. 606/213 |
| 5,192,302 | A |   | 3/1993  | Kensey et al. |
| 5,222,974 | A |   | 6/1993  | Kensey et al. |
| 5,275,616 | A |   | 1/1994  | Fowler |
| 5,292,332 | A |   | 3/1994  | Lee |
| 5,304,184 | A |   | 4/1994  | Hathaway et al. |
| 5,320,639 | A |   | 6/1994  | Rudnick |
| RE34,866  | E |   | 2/1995  | Kensey et al. |
| 5,431,639 | A |   | 7/1995  | Shaw et al. |
| 5,507,744 | A |   | 4/1996  | Tay et al. |
| 5,645,565 | A |   | 7/1997  | Rudd et al. |
| 5,810,810 | A |   | 9/1998  | Tay et al. |
| 5,871,501 | A |   | 2/1999  | Leschinsky et al. |
| 5,895,411 | A | * | 4/1999  | Irie .......................... 606/213 |
| 6,056,768 | A |   | 5/2000  | Cates et al. |

(Continued)

FOREIGN PATENT DOCUMENTS

EP     0 647 430       4/1995

(Continued)

*Primary Examiner*—Glenn K. Dawson
(74) *Attorney, Agent, or Firm*—Dergosits & Noah LLP (57) ABSTRACT

This invention relates to apparatus and methods for use in sealing a vascular puncture site and to apparatus and methods for properly locating and deploying a sealing device. The locating apparatus includes a lumen which extends from an opening in the distal region of the apparatus but located proximally of the sealing device, which lumen extends to another opening in the proximal region of the device. When the distal opening is in communication with blood in a blood vessel, blood flow through the lumen and out of the proximal opening signifies such location to the user. When the sealing device is withdrawn such that the sealing device is deployed such that it blocks the blood flow into the distal port, the user will know the location of the sealing device. In a preferred embodiment, the sealing device is then withdrawn proximally a predetermined distance to assure that no part of the sealing device extends into the blood vessel lumen. The sealing device is then detached from the delivery device.

17 Claims, 7 Drawing Sheets

U.S. PATENT DOCUMENTS

| | | |
|---|---|---|
| 6,162,240 A | 12/2000 | Cates et al. |
| 6,302,898 B1 | 10/2001 | Edwards et al. |
| 6,350,274 B1 * | 2/2002 | Li ............................ 606/213 |
| 6,368,341 B1 | 4/2002 | Abrahamson |
| 6,716,179 B2 | 4/2004 | Burbank et al. |
| 7,008,439 B1 | 3/2006 | Janzen et al. |
| 2002/0003286 A1 | 1/2002 | Ginn et al. |
| 2002/0082617 A1 | 6/2002 | Nishtala et al. |
| 2004/0019330 A1 | 1/2004 | Ashby |
| 2004/0204654 A1 | 10/2004 | Egnelov et al. |
| 2005/0065549 A1 | 3/2005 | Cates et al. |
| 2005/0085856 A1 | 4/2005 | Ginn |

FOREIGN PATENT DOCUMENTS

| | | |
|---|---|---|
| WO | WO 93/08740 | 5/1993 |
| WO | WO 03/047434 | 6/2003 |

* cited by examiner

LOCATOR AND DELIVERY DEVICE AND METHOD OF USE

RELATED APPLICATION

This patent application is a continuation-in-part of pending U.S. patent application Ser. No. 10/687,848 filed on Oct. 17, 2003, the disclosure of which is incorporated by reference herein.

FIELD OF THE INVENTION

The present invention relates generally to apparatus and methods for sealing or closing passages through tissue, and more particularly to devices for sealing punctures or other openings communicating with body lumens, such as blood vessels, and to apparatus and methods for delivering such devices.

BACKGROUND OF THE INVENTION

Catheterization and interventional procedures, such as angioplasty or stenting, generally are performed by inserting a hollow needle through a patient's skin and muscle tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

Staples and surgical clips have also been suggested for closing wounds or other openings in tissue. For example, U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. These staples, however, have a large cross-sectional profile and therefore may not be easy to deliver through a percutaneous site to close an opening in a vessel wall.

U.S. Pat. No. 6,033,427, issued to Lee, discloses a method and device for sealing internal puncture sites which, in one embodiment, uses a dual lumen bleed back system in which the distal bleed back ports are axially spaced from each other such that when the obturator is in a certain location, there will be bleed back through one of the lumens, but not through the other.

In addition, skin seals have been proposed that may be threaded into an opening in skin. For example, U.S. Pat. No. 5,645,565, issued to Rudd et al., discloses a surgical plug that may be screwed into a puncture to seal the puncture. The surgical plug includes an enlarged cap and a threaded shaft that extends from the cap. During an endoscopic procedure, the plug may be threaded into an opening through skin until the cap engages the surface of the skin. The plug is intended to seal the opening communicating with a body cavity to prevent insufflation fluid from leaking from the cavity. Such plugs, however, may only be used at the surface of the skin, and may not be introduced through tissue, for example, to seal an opening in the wall of a blood vessel or other subcutaneous region.

Various methods and means for determining the location of the distal end of a closure device have been proposed, including "bleed back" methodology such as that disclosed in U.S. Pat. No. 4,738,658 issued to Magro et al. However, prior bleed back devices have been constructed such that blood flow out of the patient continues for a longer period of time during deployment of the sealing means than would be desirable.

A further development in bleed back technology is disclosed in published U.S. patent application 2004/0019330, in which a control element having an enlarged distal end is used both to control blood flow through the blood vessel puncture and to provide an indication of the position of the distal end of an introducer sheath by withdrawing the enlarged distal end from the lumen of the blood vessel into the puncture in the wall of the blood vessel such that bleed back is, according to this published application, stopped.

Leschinsky Patent No. 5,871,501 discloses the use of an anchor on a guide wire to provide an indication of the location of the wall of a blood vessel to assist in the placement of a hemostatic material to block flow of blood out of a puncture in the vessel.

Although these and other methods and devices have been proposed for deploying a plug to prevent blood flow from a puncture in a blood vessel, a need remains for a safe and effective device and method for deploying a plug for this purpose.

SUMMARY OF INVENTION

The present invention is directed to a device which is capable of both locating a punctured blood vessel and sealing the puncture in the vessel, and to the method of using the device as well. The device makes use of a "bleed back" feature which uses a shut-off feature to indicate the location of a sealing element at an approximate desired location. A guidewire-based system is then used to more precisely locate the sealing element. In a preferred embodiment, the device comprises a delivery tube in the form of an elongate member having a lumen extending from a point in its distal region to a point in its proximal region. The lumen is connected at its proximal and distal regions to proximal and distal ports in the elongate member which create a conduit from the lumen to the outer surface of the elongate member. In this embodiment, the elongate member is also provided with a detachable sealing element which is retained within the elongate member distally of its distal port. The sealing element may be a bioabsorbable felt, a hydrogel, or other material suitable for the purpose of sealing punctures or other openings communicating with body lumens, such as blood vessels. The proximal and distal ports are spaced sufficiently far apart that the proximal port may be outside the patient's body when the distal port is within the lumen of the punctured blood vessel.

The device is also provided with an obturator in the lumen of the elongate member, which obturator has a relatively large diameter distal portion coupled to a shaft having a narrower diameter. The distal port in the elongate member is located proximally of the large diameter portion of the obturator. In this preferred embodiment, the distal portion of the obturator and the shaft have a common central lumen and an outer surface of the distal portion of the obturator is provided with a groove which is substantially parallel to the axis of the obturator. The device is also provided with a guidewire which passes through the groove on the external surface of the distal portion of the obturator and a tether which passes through the central lumen of the obturator. The guidewire has a specialized configuration at its distal end and is provided with an indicator means at its proximal region. These features facilitate the ability of the device to deploy the sealing element at a substantially precise location. Once this location is reached, the elongate member is withdrawn a short distance and the obturator is held stationary to eject the sealing element from the elongate member.

The tether, which passes through the central lumen of the obturator, is attached or coupled to the sealing element in any suitable manner, e.g., by wrapping, looping and/or tying the distal region of the tether around or to the sealing element.

In use, the device of the present invention can be used to close a puncture wound such as that in a femoral artery after a catheterization procedure has been performed. Typically, the device of the present invention will be introduced through an introducer sheath provided with a flange or other means adapted to engage the device and to prevent further distal movement and which preferably is used in the catheterization procedure. When so used, the device is passed through the introducer sheath until the sealing element at the distal end of the obturator and the distal port in the elongate member are within the lumen of the femoral artery. The user will know when this has occurred when the engaging means on the introducer sheath arrests further distal movement by the device. When this occurs, blood will emerge from the proximal port because when the distal port reaches the lumen of a blood vessel, such as the femoral artery, blood will flow from the blood vessel, through the distal port, into and through the lumen in the elongate member and out of the proximal port.

Next, the device and sheath are withdrawn together a short distance such that the distal port is no longer within the lumen of the femoral artery and the flow of blood is substantially blocked from reaching the distal port by the patient's tissue and the sealing element.

The user will know when the sealing element is close to the desired position once it causes the blood flow out of the proximal port to cease or substantially diminish. At this point, the sealing element is at approximately the desired location. The device is then withdrawn until a disc attached to the proximal portion of the delivery tube comes into contact with a disc attached to the proximal portion of the guidewire, at which point the sealing element is in the final deployment position.

The disc attached to the guidewire and the disc attached to the delivery tube are spaced a short distance apart and permit a more precise positioning of the sealing element than would otherwise be possible. It is to be noted, however, that the use of such discs is preferred, but that other structures can be used to accomplish the same purpose.

The guidewire is then withdrawn into the guidewire tube in the groove in the obturator while holding the remainder of the device in place. At this time, the sealing instrument is at the desired location and can be deployed by withdrawing the elongate member a short distance, while holding the obturator in place, as described above. After deployment, the distal end of the obturator will be substantially at the distal end of the elongate member. The distal end of the guidewire will be in the lumen of the guidewire tube and the elongate member, obturator and guidewire may then be withdrawn from the patient as a unit. The tether will remain coupled to the sealing element and can be used to retrieve the sealing element should it become dislodged from the tract in the tissue leading to the puncture in the blood vessel.

If the device of the present invention is delivered through an introducer sheath, it is preferred to provide a coupling device such that the sheath and the device will become attached to each other when the distal port of the elongate member is within the lumen of the blood vessel. If this is done, the withdrawal of the device and the sheath as a unit will be facilitated as will the maintenance of the distal port at a location distal to the distal end of the sheath.

In the preferred embodiment, the sealing element is fabricated from an expandable material such as a felt made from strands of polyglycolic acid (PGA) which, because of its felt structure, then expands to assure an effective closure of the puncture wound. Alternatively, the sealing element may be fabricated from a hydrogel, such as hydroxypropyl cellulose (HPC) microporous hydrogel The seal may also be coated with or otherwise provided with a hemostatic material which will promote clotting.

The foregoing description has been directed to sealing a puncture wound in the femoral artery, but it is to be understood that the device of the present invention can be used to locate the lumens of other blood vessels and to seal puncture wounds in them. With that understanding, we turn to a more detailed description of the invention.

DETAILED DESCRIPTION OF THE INVENTION

Figure 1:
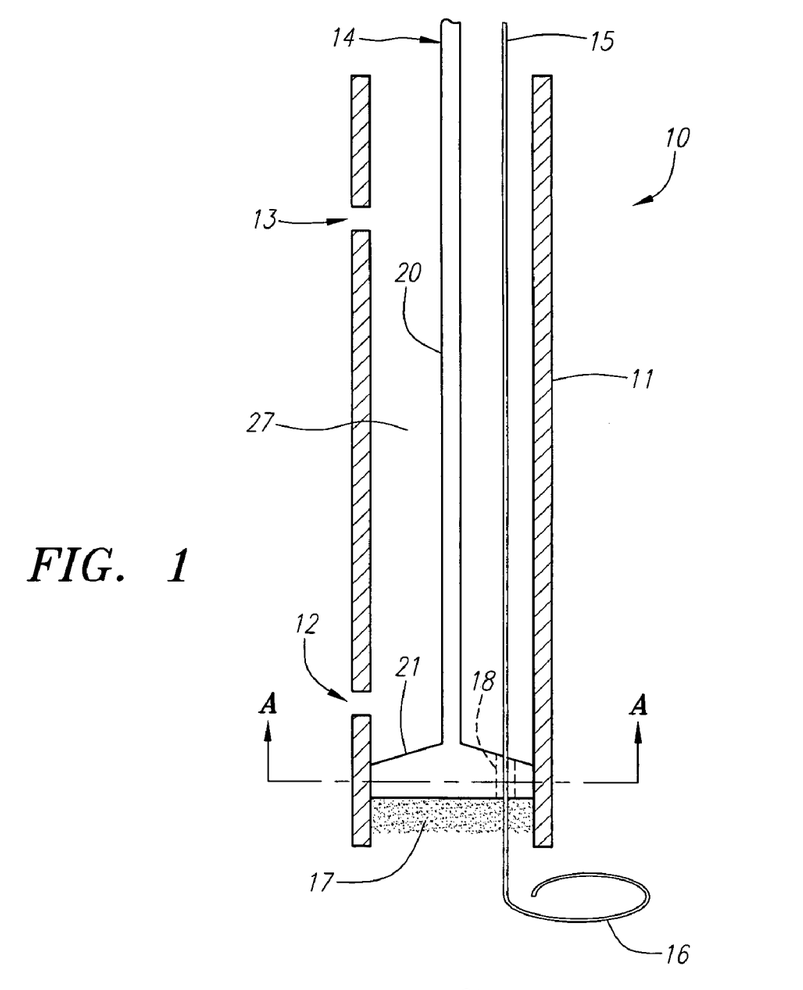
FIG. 1 is a schematic illustration of the device of the present invention.

FIG. 1 illustrates in a somewhat schematic form many of the features of the device of the present invention. The device 10 includes a delivery tube 11 which is provided with a distal port 12 and a proximal port 13. An obturator 14 is housed within the delivery tube 11 and comprises a shaft 20 and a larger diameter distal portion 21. The device 10 is also provided with a guidewire 15 which has a transversely extending distal portion 16. The device is also provided with a sealing element 17 which is preferably formed from a felt, hydrogel, or other material suitable for use in sealing punctures or other openings communicating with body lumens, such as blood vessels.

Figure 2:
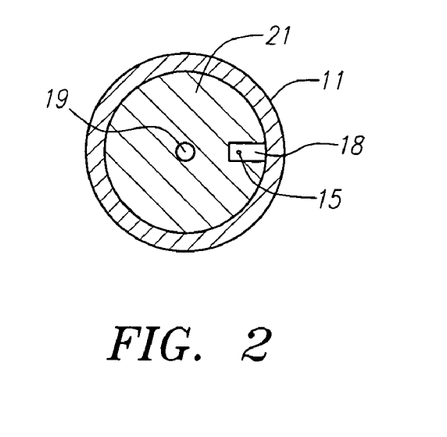
FIG. 2 is a cross-sectional view of the device illustrated in FIG. 1, taken on line A-A.

FIG. 2 is a cross-sectional view of the device shown in FIG. 1 taken on line A-A. As can be seen from FIG. 2, the distal portion 21 of the obturator 14 is provided with a groove 18 which serves as a passageway for the guidewire 15. In addition, the obturator 14 is provided with a lumen 19 (not shown in FIG. 1) which extends from its distal end to its proximal end and which serves as a passageway for a tether (also not shown).

Figure 3:
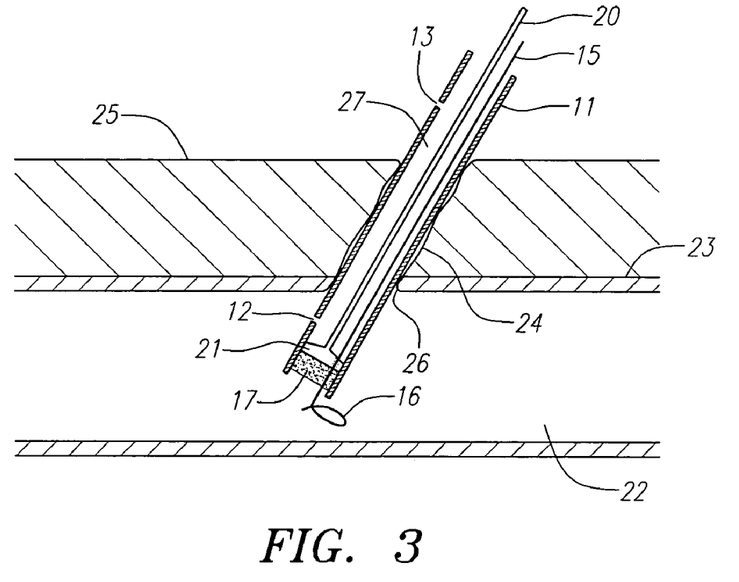
FIG. 3 illustrates the device of the present invention having its distal end inserted into the lumen of a blood vessel.

FIG. 3 illustrates the device 10 having its distal portion inserted into the lumen 22 of a blood vessel 23. As can be seen, the device extends through a tract 24 which extends through the tissue from the skin 25 of the patient to a puncture 26 in the wall of the blood vessel. When so positioned, the bleed back feature of the device, which comprises the distal port 12 in the delivery tube 11, the lumen 27 of the delivery tube 11, and the proximal port 13 of the delivery tube 11, functions to indicate to the user that the distal portion of the delivery tube 11 is located in the blood vessel lumen by reason of the visible flow of blood out of the proximal port 13.

Figure 4:
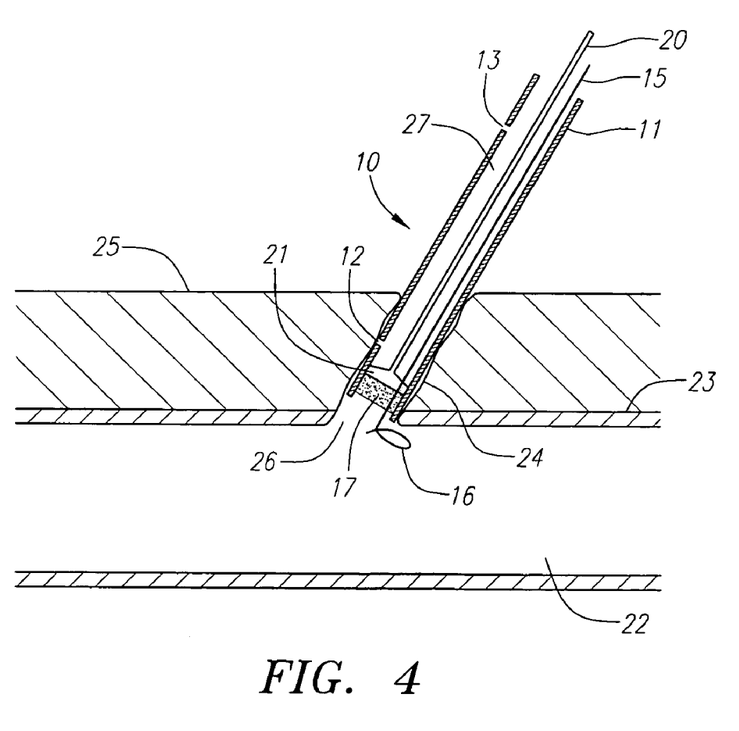
FIG. 4 shows the device of the present invention when it has been substantially withdrawn from the lumen of a blood vessel.

FIG. 4 illustrates the device 10 after its distal portion including the distal port 12 has been withdrawn from the interior of the lumen 22 of the vessel 23. When the device is in the position illustrated in FIG. 4, the tissue of the patient and the sealing material 17 have substantially diminished or prevented blood flow from reaching the distal port 12 and the proximal port 13. Accordingly, the user will know from the substantial absence of blood flowing from the port 13 that the sealing material 17 is in approximately the appropriate location for deployment. However, before the sealing material 17 is deployed, additional positioning steps are preferably taken.

Referring to FIG. 4, it can be seen that the transversely extending distal portion 16 of the guide wire is not in contact with the vessel wall at this stage of withdrawal of the device 10.

Figure 5:
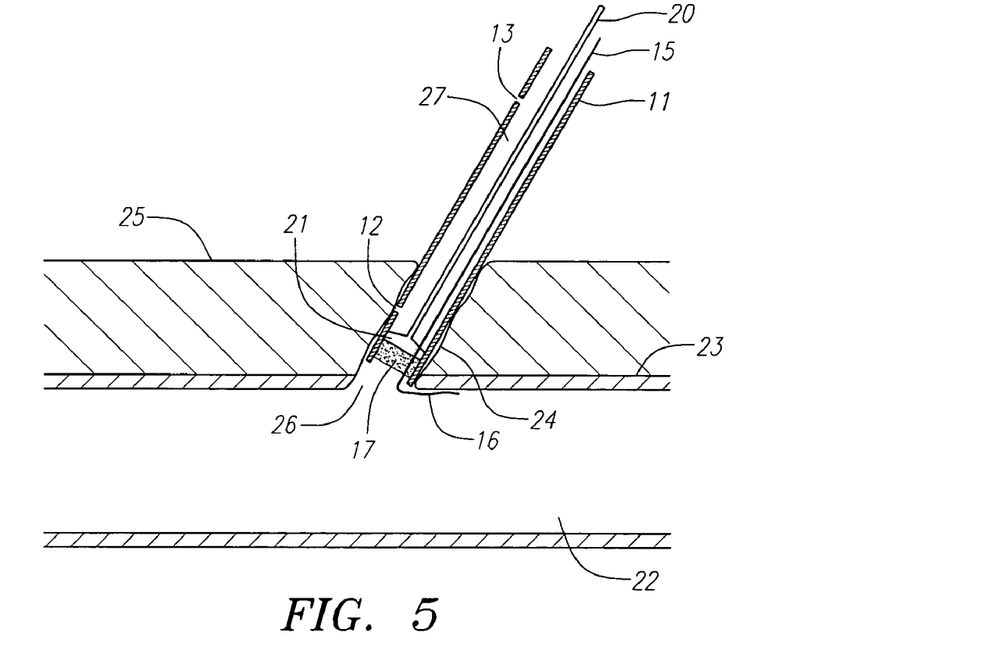
FIG. 5 shows the device of the present invention when the seal has been properly positioned.

Referring next to FIG. 5, it can be seen that the distal portion 16 of the guidewire has been brought into contact with the vessel wall 23 and that, in addition, the distal portion 16 of the guidewire has been reconfigured by reason of the pressure exerted by the wall on that distal portion 16. This contact between the distal portion of the guide wire and the vessel wall can be felt by the user because of the resistance to further proximal movement of the guidewire 15. This contact may also be confirmed by viewing the deformation of the distal portion 16 of the guidewire by suitable means, such as by fluoroscopy. This occurrence may be used to achieve final positioning of the device for deployment of the sealing element 17, as described more fully below.

Figure 6:
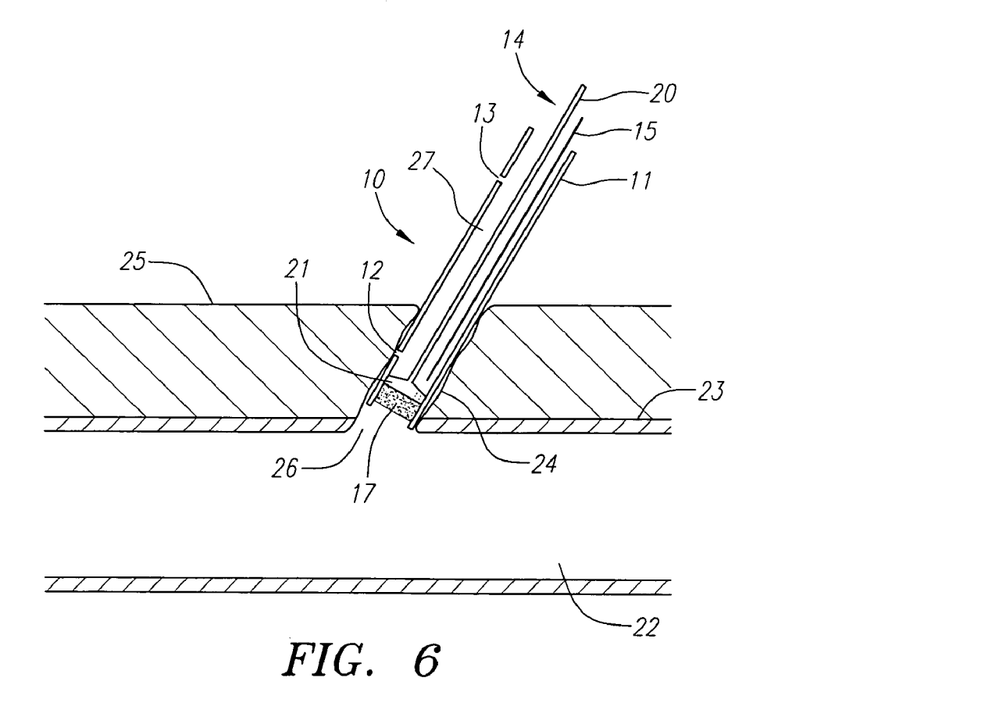
FIG. 6 shows the device of the present invention after the seal has been ejected into the tissue tract.

As shown in FIG. 6, the sealing material 17 is deployed by withdrawing the delivery tube 11 proximally while at the same time holding the obturator 14 stationary. This causes the sealing element 17 to be ejected from the tube 11 and to take its desired position in the vessel tract 24 proximal to the puncture 26. The guide wire 15 is also withdrawn proximally such that its distal portion 16 passes through the groove 18 and resides in the lumen 27 of the delivery tube 11, or, preferably, in a guidewire tube 34 extending through the length of the lumen 27 (see FIG. 8). Preferably, the distal end of the tube 11 will be flush with the distal end of enlarged portion 21 of the obturator 14. The entire device 10 may then be removed from the patient by withdrawing it from the tract 24. Preferably, a tether (not shown) which extends through the central lumen 19 of the obturator 14 is provided and is tied or otherwise suitably attached to the sealing element 17. The tether serves to give the user at least a measure of control over the sealing element 17 in the event that there is any need to withdraw the sealing element 17 from the patient. This may be done simply by pulling proximally on the tether until the sealing element 17 is removed.

Figures 7, 8:
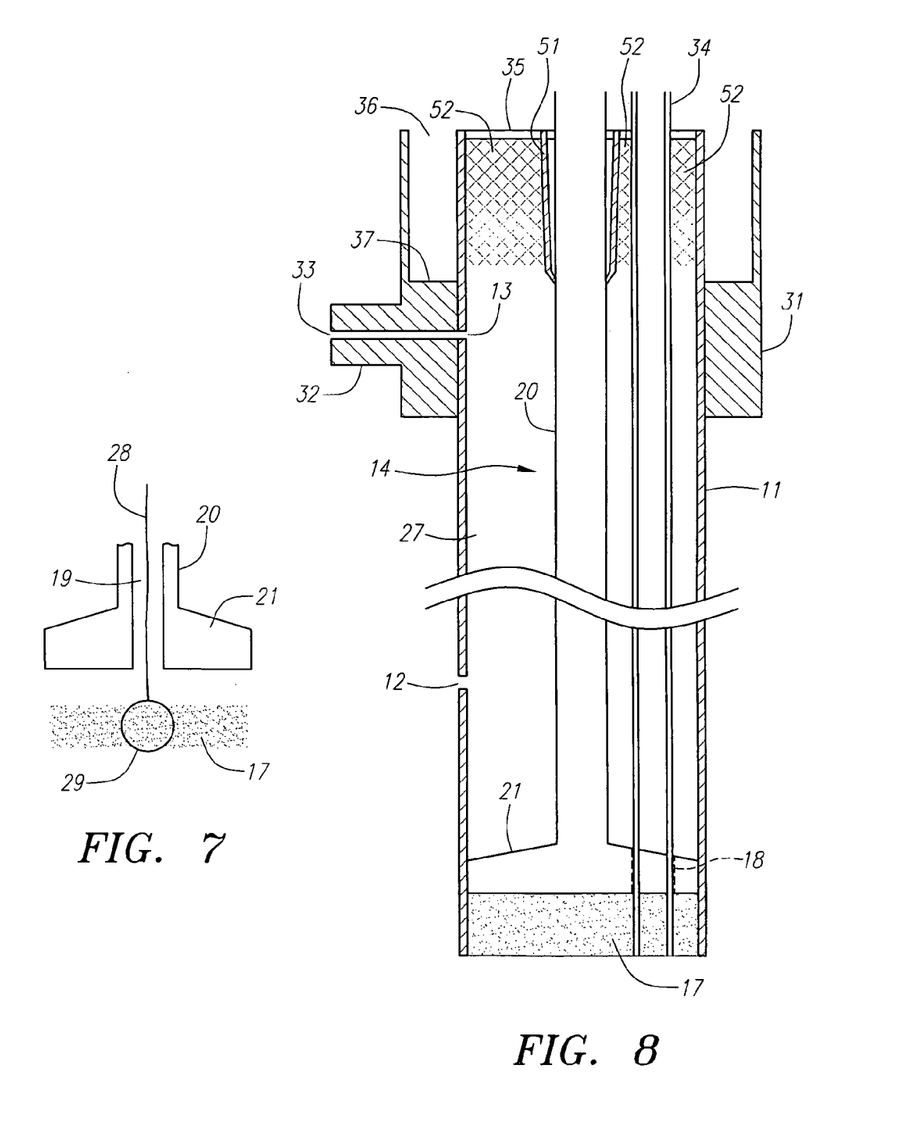
FIG. 7 illustrates the tether feature of the device shown in FIG. 1.
FIG. 8 illustrates the device of the present invention with more detail at its proximal end.

The relationship between the tether 28 which has its distal portion looped around the sealing element 17 is shown diagrammatically in FIG. 7, which also shows the distal portion 21 and the shaft 20 of the obturator 14 having its central lumen 19 extending therethrough. As noted above, the tether 28 may be secured to the sealing element 17 by tying, looping, or any other suitable means. The representation shown in FIG. 7 is for illustrative purposes.

Referring now to FIG. 8, the device of the present invention is illustrated in somewhat more detail with regard to its proximal structure. FIG. 8 shows the delivery tube 11 which is provided with the distal port 12 and proximal port 13 and which houses the shaft 20 and the distal portion 21 of the obturator in its lumen 27. The delivery tube 11 is also provided with a guidewire tube 34 which serves as a passage for the guidewire from the proximal end of the device through the groove 18 in the distal portion 21 of the obturator. The sealing element 17 is also shown.

The actuator 31, which is bonded or otherwise suitably attached to the delivery tube 11, is also shown. The actuator 31 is provided with a knob 32 that has a lumen 33 which is aligned with the proximal port 13 in the delivery tube 11. The knob 32 can be used to move the delivery tube 11 proximally and distally. In use, the actuator 31 is moved proximally while holding the obturator 14 stationary such that the sealing element 17 is ejected from the delivery tube 11 once the delivery tube has been properly located. A cap 35 is provided with an aperture through which the shaft 20 of the obturator 14 can slide. A length of necked tubing 51 is provided surrounding the shaft 20 to provide a slidable seal. The cap 35 is also provided with an aperture for the guide wire tube 34, but the guide wire tube 34 is bonded or otherwise suitably attached to the cap 35 such that movement of the actuator 31 will cause the delivery tube 11 and the guide wire tube 34 to move as a unit. Adhesive material 52 is provided near the proximal end of the delivery tube 11 to maintain the relative positions and seal the necked tubing 51 and guidewire tube 34 relative to the delivery tube 11.

The actuator 31 is also provided with a recess 36 which is preferably annular in configuration. The recess 36 terminates at a floor 37 which, as explained in more detail with regard to other drawings, functions as a seat for a spring.

Figure 9:
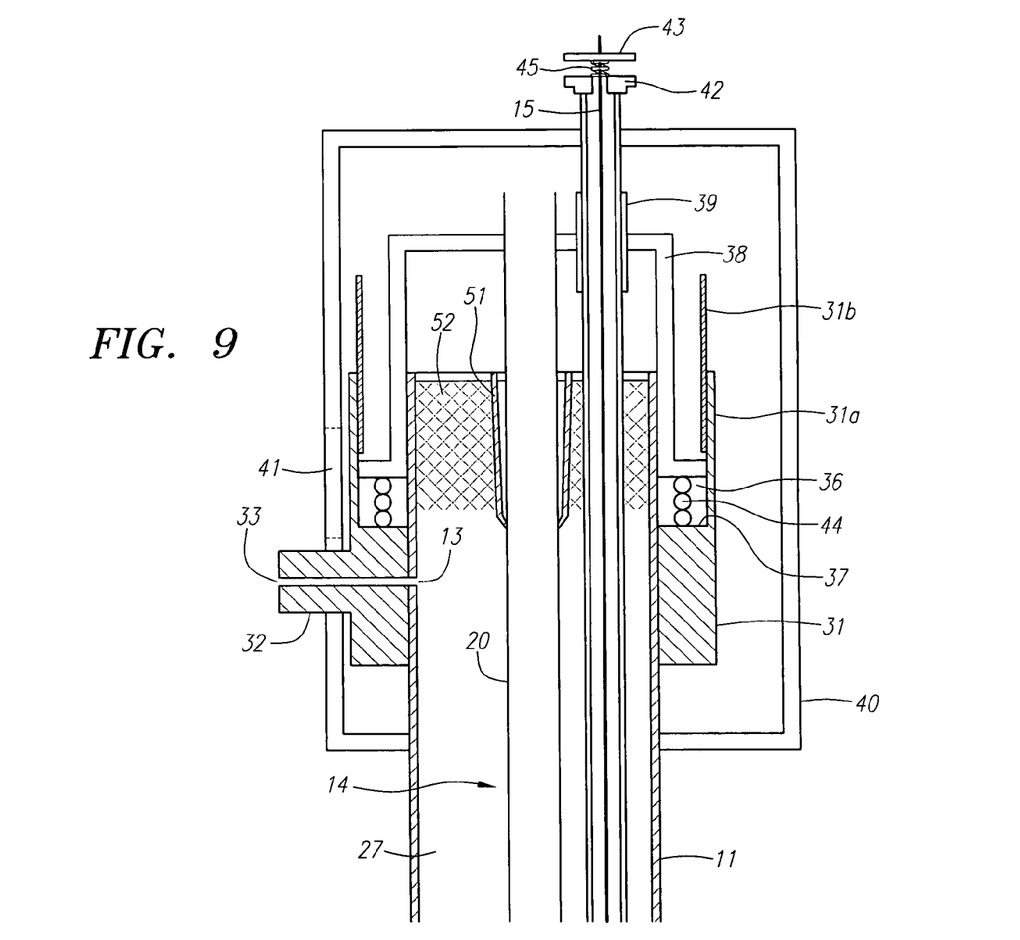
FIG. 9 illustrates further detail of the proximal end of the device.

FIG. 9 further illustrates the proximal region of the device and, in addition to the elements shown in FIG. 8, shows a button 38 in the recess 36 with a spring 38 biasing the button 36 in a proximal direction. The proximal end of the button 38 is provided with a tube 39 through which the guidewire tube 34 can slide. Also shown is a handle 40 which surrounds the actuator 31 and the button 38. The handle 40 is provided with an L-shaped slot 41, which is more completely illustrated in FIG. 10, in which the knob 32 is able to move. This L-shaped slot is partially shown as element 41 in FIG. 9. The proximal portion of the guidewire tube 34, which is fixed to the actuator 31, is provided with an actuator disc 42. Proximal to the actuator disc 42 is a guidewire disc 43 which is attached to the guidewire 15. The actuator disc 42 and the guidewire disc 43 are separated by a spring 45.

Figure 10:
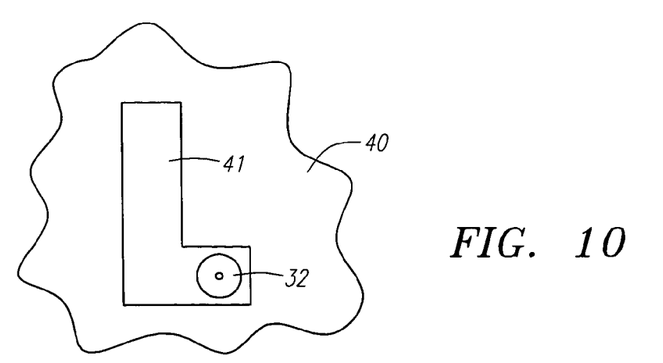
FIG. 10 illustrates a slot in the handle of the device.

The L-shaped slot 41 in the handle 40 is shown in more detail in FIG. 10. As can be seen from that Figure, the knob 32 can move both transverse to the longitudinal axis of the device in the shorter leg of the slot and in an axial direction in the longer leg of the slot.

Figure 11:
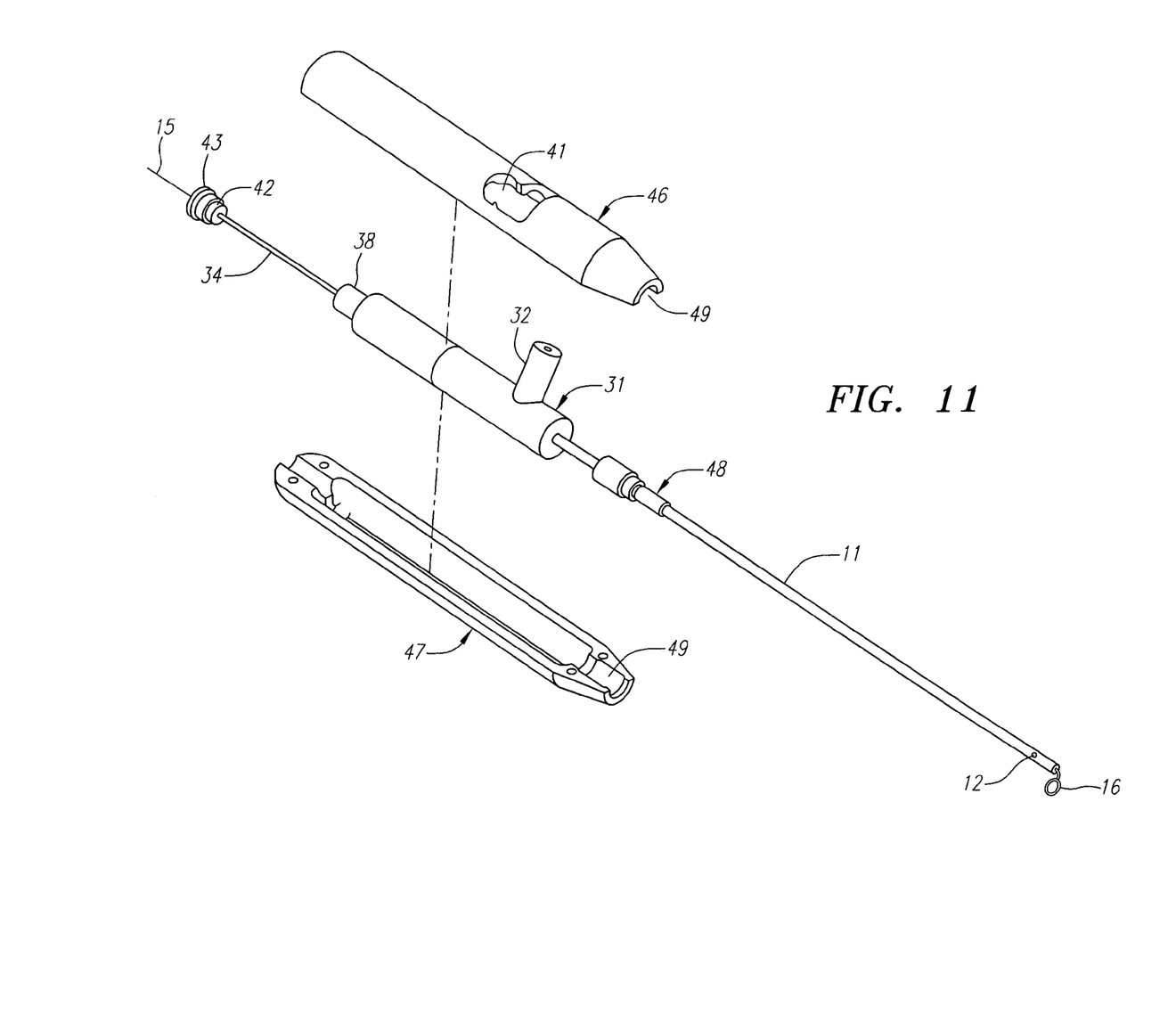
FIG. 11 illustrates an exploded perspective view of the device of the present invention.

FIG. 11 is an exploded perspective view of an embodiment of the device of the present invention. As here illustrated; it can be seen that handle 40 is comprised of an upper half 46 and a lower half 47. The handle upper half 46 contains the L-shaped slot 41. The actuator 31 having the knob 32 and the button 38 are also shown, with the knob 32 being received and retained in the L-shaped slot 41. The delivery tube 11 with the distal port 12 together with the distal portion of the guidewire 44 comprise the distal portion of the device. The delivery tube 11 is provided with a collar 48 which extends into the distal recess 49 in the handle 40 when the upper and lower handle halves 46 and 47 are joined together. The actuator disc 42 is attached to the guidewire tube 34 near its proximal end, while the guidewire disc 43 is attached to the guidewire at a point proximal to the actuator disc.

Figure 12A:
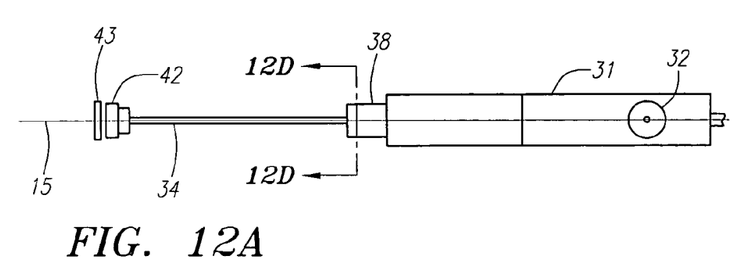
FIGS. 12A and 12B illustrate portions of the device shown in FIG. 11, with additional detail at its proximal end.
Figure 12B:
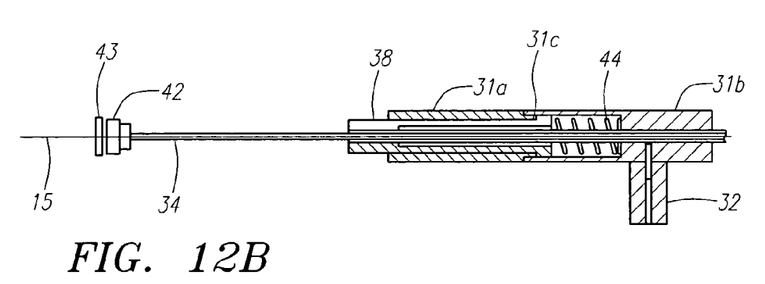

Turning to FIGS. 12A-D, additional detail is shown relating to the actuator 31 and the actuator disc 42 and guidewire disc 43. In FIG. 12A-B, the actuator 31 is shown, having the knob 32 located at a distal portion and the button 38 at its proximal end. The actuator 31 comprises two parts, a proximal portion 31a and a distal portion 31b (see FIG. 12B). The proximal portion 31a of the actuator forms an internal shoulder 31c that limits proximal movement of the button 38. The spring 44 (FIG. 12B) biases the button in the proximal direction. The guidewire tube 34 extends proximally from the actuator 31, with the guidewire 15 located inside the lumen of the guidewire tube 34. The actuator disc 42 is attached to the proximal end of the guidewire tube 34, and the guidewire disc 43 is attached to the guidewire 14 at a point proximal to the actuator disc 42.

Figure 12C:
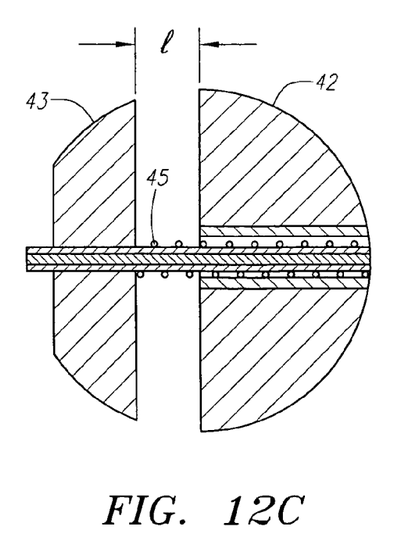
FIG. 12C illustrates further detail of components of a precise positioning feature.

Referring to FIG. 12C, a disc spring 45 is provided between the actuator disc 42 and the guidewire disc 43. The disc spring 45 provides a force that tends to separate the two discs 42, 43, i.e., the disc spring 45 biases the actuator disc 42 distally and biases the guidewire disc 43 proximally, relative to one another.

Figure 12D:
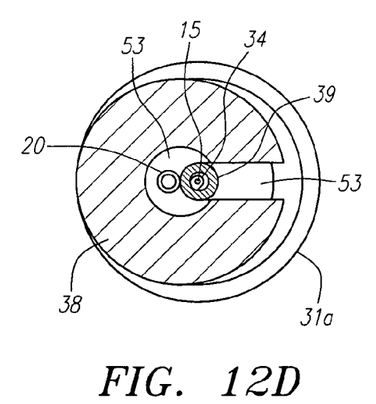
FIG. 12D illustrates a cross-sectional view of the device illustrated in FIG. 12A, taken on line D-D.

FIG. 12D provides additional detail relating to the proximal portion of the device. As shown, the button 38 has a lumen 53 that is used to inject the adhesive material 52 described above in relation to FIG. 9. The obturator shaft 20 is attached to the button 38, as is the tube 39 through which the guidewire tube 34 and guidewire 15 are able to slide. The proximal portion of the actuator 31a is shown, and is described more fully above.

Additional detail concerning the operation of the actuator disc 42 and guidewire disc 43 will now be described. The actuator disc 42 and guidewire disc 43 are used to provide final, precise positioning of the sealing element 17 in the tract 24 formed in the tissue of the patient. As described previously, the guidewire disc 43 is attached to a proximal portion of the guidewire 14, whereas the actuator disc 42 is attached to the guidewire tube 34, which is, in turn, attached to the actuator 31. The two discs 42, 43 are separated by a small distance, 1, as shown in FIG. 12C. When the device 10 is being withdrawn from the lumen of the vessel, as described above, the distal portion 16 of the guidewire engages the vessel wall 23 at the point during withdrawal that the distal end of the device 10 is withdrawn from the vessel, as shown, for example, in FIG. 5. At this point, the bleedback feature will be in a condition that no substantial bleedback is taking place, indicating that the device is near the location at which the sealing element 17 is to be deployed. Continued withdrawal of the device will cause the guidewire 15 to remain relatively stationary, due to the engagement of the guidewire distal portion 16 with the vessel wall. At the same time, the actuator 31, the actuator disc 43, and the remaining portions of the device 10 will continue to move proximally. The final deployment position is indicated when the actuator disc 43 engages the guidewire disc 42, i.e., when the device has been withdrawn an additional distance—1—from the point at which the guidewire distal portion 16 engages the vessel wall. At this point, the sealing element 17 is deployed.

As described above, deployment of the sealing element is achieved by causing proximal movement of the delivery tube 11 relative to the obturator 14. This is achieved by sliding the knob 32 axially in the L-shaped slot 41. Because the knob 32 is coupled with the actuator 31, this axial movement causes the actuator 31 and the delivery tube 11 to advance proximally. At the same time, the obturator 14 is held in place, thereby deploying the sealing element 17 in the selected location. The actuator 31 is able to move proximally within the handle 40 against the spring force of the button spring 44, as the proximal end of the button 38 engages an internal surface of the handle 40. In this way, the delivery tube 11, which is attached to the actuator 31, is able to move axially relative to the actuator 14.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A device for sealing a puncture in the wall of a body lumen comprising
an elongate member having a lumen therein and a distal port in a distal region thereof and a proximal port in a proximal region thereof, each of said ports communicating with said lumen in said elongate member,
an obturator housed in said elongate member, a distal portion of said obturator having a relatively large external dimension which is coupled to a shaft which extends proximally from the distal portion thereof, said obturator being provided with a central lumen which extends from the distal end of said obturator proximally through said shaft, a groove in the external surface of the distal portion of the obturator, and
a guidewire extending through said lumen in said elongate member and through said groove, said guidewire having a distal region capable of resisting proximal movement, but being sufficiently flexible to be withdrawn proximally through said groove.

2. The device of claim 1 which is provided with a sealing element in the distal region of the elongate member which is located distally of the distal and of the obturator.

3. The device of claim 2, further comprising
a guidewire tube extending through said lumen in said elongate member, wherein said guidewire is retained within said guidewire tube.

4. The device of claim 3, further comprising
a means for positioning said sealing element in a location near the puncture in the wall of the body lumen.

5. The device of claim 4, wherein said means for positioning comprises a first member attached to said guidewire tube and a second member attached to said guidewire, said first and second members having a spatial relationship that is used to position said sealing element.

6. The device of claim 2, further comprising
a tether extending through the central lumen of said obturator and attached to the sealing element.

7. The device of claim 1, further comprising
an actuator coupled to said elongate member, said actuator adapted to facilitate movement of said elongate member relative to said obturator.

8. A method for substantially sealing an opening in a body lumen, comprising:
inserting at least a distal end of a closure device through a tissue tract into said body lumen,
confirming that at least the distal end of the closure device is in said body lumen by observing blood flow through a lumen in said closure device,
withdrawing the distal end of the closure device from the body lumen such that the closure device remains in the tissue tract, and
deploying a sealing element from said lumen of said closure device.

9. The method of claim 8, wherein said confirming step comprises observing said blood flow out of a proximal port in said lumen of said closure device.

10. The method of claim 9, wherein said blood flow is substantially stopped after a distal port located near the distal end of the closure device is withdrawn from said body lumen.

11. The method of claim 8, further comprising:
positioning said distal end of the closure device at a location in the tissue tract, said location determined at least in part by engaging a portion of a guidewire extending through the closure device to a portion of said body lumen.

12. The method of claim 11, wherein said positioning step comprises:
engaging a distal end portion of the guidewire with a wall of said body lumen, and withdrawing the closure device a predetermined distance after the distal end portion of the guidewire is engaged with the wall of the body lumen.

13. The method of claim 12, further comprising:
confirming that the closure device is withdrawn by the predetermined distance by observing a first member attached to a guidewire tube on said closure device and a second member attached to a guidewire.

14. The method of claim 8, wherein said deploying step comprises moving an elongate member of said closure device proximally while an obturator of said device is held in place, thereby releasing said sealing element from the distal end of the closure device.

15. A device for sealing a puncture in a wall of a body lumen comprising:
an elongate member having a distal port, a proximal port, and a passage connecting said distal and proximal ports,
an obturator extending through at least a portion of said elongate member, said obturator having a distal portion adapted to selectively prevent movement of a sealing member in a proximal direction when the elongate member is withdrawn proximally to release said sealing member to seal the puncture of the wall of the body lumen;
a guidewire extending through said elongate member, said guidewire having a transversely disposed portion at a distal region;
a guidewire tube extending through a lumen in said elongate member, wherein said guidewire is retained within said guidewire tube; and
means for positioning said sealing element in a location near the puncture in the wall of the body lumen.

16. The device of claim 15, wherein said means for positioning comprises a first member attached to said guidewire tube and a second member attached to said guidewire, said first member and said second member having a spatial relationship that is used to position said sealing element.

17. A device for sealing a puncture in a wall of a body lumen comprising:
an elongate member having a distal port, a proximal port, and a passage connecting said distal and proximal ports,
an obturator extending through at least a portion of said elongate member, said obturator having a distal portion adapted to selectively prevent movement of a sealing member in a proximal direction when the elongate member is withdrawn proximally to release said sealing member to seal the puncture of the wall of the body lumen;
a guidewire extending through said elongate member, said guidewire having a transversely disposed portion at a distal region; and
a central lumen which extends from the distal end of the obturator, and a tether extending through the central lumen of said obturator and attached to the sealing element.

* * * * *